(12) United States Patent
Ortmaier et al.

(10) Patent No.: US 8,548,629 B2
(45) Date of Patent: Oct. 1, 2013

(54) X-RAY DEVICE AND MEDICAL WORKPLACE

(75) Inventors: Tobias Ortmaier, Hemmingen (DE); Peter Heiligensetzer, Augsburg (DE)

(73) Assignee: KUKA Laboratories GmbH, Augsburg (DE)

( * ) Notice: Subject to any disclaimer, the term of this patent is extended or adjusted under 35 U.S.C. 154(b) by 340 days.

(21) Appl. No.: 12/988,178

(22) PCT Filed: Apr. 17, 2009

(86) PCT No.: PCT/EP2009/054576
§ 371 (c)(1),
(2), (4) Date: Nov. 16, 2010

(87) PCT Pub. No.: WO2009/127713
PCT Pub. Date: Oct. 22, 2009

(65) Prior Publication Data
US 2011/0054688 A1    Mar. 3, 2011

(30) Foreign Application Priority Data

Apr. 17, 2008  (DE) .......................... 10 2008 019 345

(51) Int. Cl.
*G06F 19/00*  (2011.01)
*A61G 13/04*  (2006.01)
(52) U.S. Cl.
USPC ............... 700/255; 378/197; 378/95; 378/98; 600/427; 600/410; 5/601; 324/662
(58) Field of Classification Search
USPC ............... 378/197, 95, 98.2, 68, 69, 35, 209; 600/427, 410; 5/601; 324/662, 658; 700/255
See application file for complete search history.

(56) References Cited

U.S. PATENT DOCUMENTS

| 4,063,073 | A | 12/1977 | Strayer |
| 5,485,502 | A | 1/1996 | Hinton et al. |
| 6,637,936 | B2 * | 10/2003 | Crain et al. ................... 378/197 |

(Continued)

FOREIGN PATENT DOCUMENTS

| DE | 201 09 313 U1 | 9/2001 |
| DE | 102 00 534 A1 | 7/2003 |

(Continued)

OTHER PUBLICATIONS

European Patent Office; Search Report in International Patent Application No. PCT/EP2009/054576 dated Oct. 19, 2009, 6 pages.
Tim Schroder; "High-Sensitivity Robot Arms", Medical Solutions, Oct. 2006, pp. 62-64.

(Continued)

*Primary Examiner* — Ronnie Mancho
(74) *Attorney, Agent, or Firm* — Wood, Herron & Evans, LLP

(57) ABSTRACT

The invention relates to an X-ray device (2) for a medical workplace (1, 21). The X-ray device (2) comprises a robot (R) with a plurality of axes (9), a control device (10) for controlling the axes (9) for movement of the robot (R), and a fastening device (8), and a support device (11) disposed at the fastening device (8), said support device comprising an X-ray radiation source (12) and an X-ray radiation receiver (14). A 3D model (15, 15a) of the robot (R) and the support device (11) provided is stored in the control device (10), said 3D model modeling the spatial extension of the robot (R) and the support device (11) during movement of the robot (R). The 3D model (15,15a) also models the spatial extension of at least one other device (3, 4, R2) of the medical workplace (1, 21) and/or of a living organism (5) located within the medical workplace (1, 21). The control device (10) recognizes a potential collision of the X-ray device (2) with the other device (3, 4, R2) and/or the living organism (5) based on the 3D model (15,15a) and prompts the robot (R) to take action to avoid the potential collision.

10 Claims, 2 Drawing Sheets

(56) References Cited

U.S. PATENT DOCUMENTS

Figure 1:
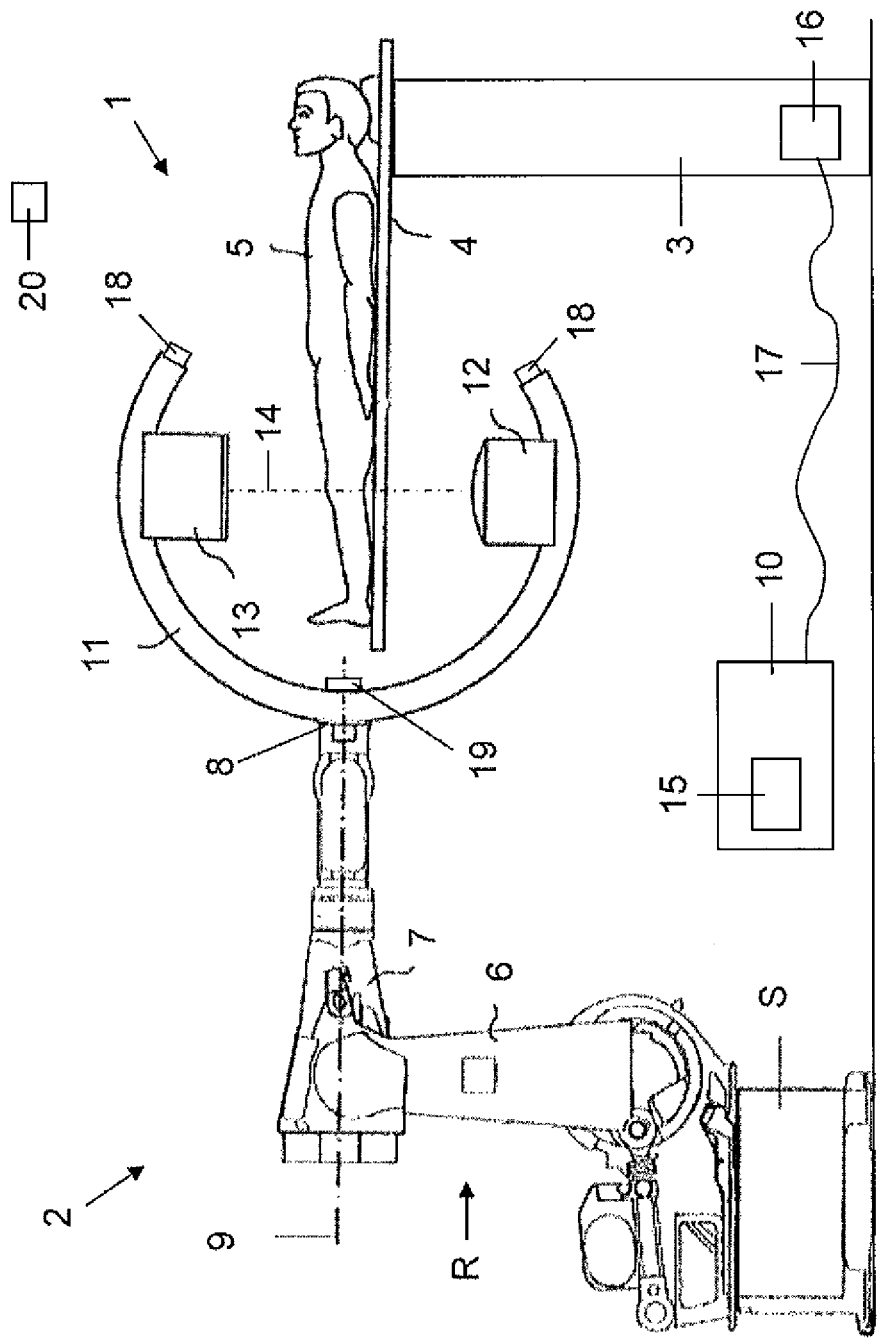

| | | |
|---|---|---|
| 7,570,064 B2 * | 8/2009 | Roziere .................. 324/662 |
| 7,741,623 B2 | 6/2010 | Sommer |
| 7,742,562 B2 * | 6/2010 | Weber .................... 378/68 |
| 7,855,656 B2 | 12/2010 | Maschke |
| 7,860,550 B2 * | 12/2010 | Saracen et al. ............ 600/410 |
| 8,160,205 B2 * | 4/2012 | Saracen et al. ............ 378/69 |
| 2008/0234865 A1 | 9/2008 | Sommer |

FOREIGN PATENT DOCUMENTS

| | | |
|---|---|---|
| DE | 10 2005 012 700 A1 | 9/2006 |
| DE | 10 2005 041 606 A1 | 3/2007 |
| EP | 0 220 501 A1 | 5/1987 |
| EP | 0 087 198 B1 | 11/1987 |
| FR | 2115423 A | 7/1972 |
| FR | 2240884 A | 3/1975 |

* cited by examiner

X-RAY DEVICE AND MEDICAL WORKPLACE

The invention relates to an X-ray device and a medical workstation.

Robots in general are working machines, which can be equipped with tools for automatic handling and/or processing of objects, and are programmable in a plurality of motion axes, for example with regard to orientation, position and process sequence. Robots normally have programmable controllers (controlling devices) which control the sequences of motions of the robot during operation.

Robots are being utilized increasingly in medical technology, for example as carriers of patient support and positioning systems and diagnosis systems, such as X-ray devices. Here the robot moves in direct or immediate contact with persons, for example a doctor or a patient, without intervening protective devices, as is normal in particular with industrial applications. Safety technology plays a decisive role in preventing the robot from accidentally injuring a person. For example, the motion of the robot can be monitored using secure technology. The monitoring includes, among other things, fail-safe angle sensors, redundant calculation of position, velocity and acceleration, and reliable monitoring of the derived values.

DE 10 2005 012 700 A1 discloses an X-ray device having a robot with six axes of rotation and a U-shaped carrier attached to the robot, on which an X-ray source and an X-ray detector are situated.

DE 10 2005 041 606 A1 discloses a patient positioning device for positioning a patient in an irradiation position for a radiation therapy system. The patient positioning device includes a patient holding module, and a positioning arm that moves the patient holding module, whose motion is controlled by a therapy control center. Pressure sensors are situated on the patient holding module, so that a patient moved by means of the patient holding module is protected against unwanted effects by interrupting the actuation of the positioning arm when one of the pressure sensors is activated.

One object of the invention is to specify an X-ray device having a robot and a carrying device situated on the robot for a medical workstation that includes an X-ray source and an X-ray receiver, so that at least the danger of a collision between the X-ray device and at least one additional device of the medical workstation and/or a living organism present at the workstation is reduced.

Another object of the invention is to specify a medical workstation having an X-ray device that has a robot and a carrying device situated on the robot that includes an X-ray source and an X-ray receiver, so that at least the danger of a collision between the X-ray device and at least one additional device of the medical workstation and/or a living organism present at the workstation is reduced.

The problem of the invention is solved by an X-ray device for a medical workstation having a robot having a plurality of axes, a control device that is set up to actuate the axes for a motion of the robot, and an attaching device, and a carrying device situated on the attaching device, having an X-ray source and an X-ray receiver, wherein a 3D model of the robot with positioned carrying device is stored in the control device, which models the spatial extension of the robot with positioned carrying device while the robot is in motion, the 3D model also models the spatial extension of at least one additional device of the medical workstation and/or of a living organism present within the medical workstation, and the control device detects a potential collision of the X-ray device with the additional device and/or the living organism on the basis of the 3D model and causes the robot to initiate an action to prevent the potential collision.

Accordingly, the X-ray device according to the invention has the robot with a plurality of axes which are actuated by the control device during operation. This is realized for example in that the robot has drives which are actuated by the control device so that the drives move the axes. The drives are for example electric drives.

The robot also has the attaching device, for example a flange, on which the carrying device is situated. The carrying device, which is designed for example in the shape of a C or a U, has in turn the X-ray source and the X-ray receiver. The X-ray source and the x-ray receiver are situated on the carrying device in such a way that when the x-ray device according to the invention is in operation, an X-ray beam produced by the X-ray source strikes a living organism, is partially attenuated by that organism, and arrives at the X-ray receiver. The X-ray receiver, which is for example an X-ray image intensifier or flat screen detector, converts the incoming X-ray beam for example into electrical signals whose distribution can be depicted as an X-ray image.

The X-ray device according to the invention is intended for a medical workstation which has, in addition to the X-ray device, at least the additional device. The additional device is for example an additional medical technology device such as a lithotripter or an ultrasound device or, as provided according to one embodiment of the X-ray device according to the invention, a patient table, in particular one that is height-adjustable.

An additional aspect of the invention relates to a medical workstation that has the X-ray device according to the invention and the patient table, especially one that is height-adjustable, where the 3D model also models the spatial extension of the patient table, so that the control device recognizes a potential collision of the X-ray device with the patient table on the basis of the 3D model and causes the robot to initiate an action to prevent the potential collision.

When the X-ray device according to the invention is in operation, the robot moves the carrying device, for example in order to record one or more X-ray images of a living organism. The living organism can lie or sit for example on the patient table, and the robot automatically moves the carrying device to the living organism in order to record the X-ray image or images. The X-ray device according to the invention can be designed in particular in such a way that it records a series of 2D projections of the living organism, from which a volume record of the living organism can be computed in a manner known to a person skilled in the art. If the carrying device is designed as a C-shaped arc, the robot can shift the C-shaped arc while recording the 2D projections, in particular along its perimeter (orbital motion) or during an angulation movement. Other motions are also possible because of the robot.

In order to prevent a collision with the additional device of the medical workstation and/or the living organism when the robot is moving, the 3D model is stored in the control device. The 3D model models the spatial dimensions of the robot and of the carrying device that has the X-ray source and the X-ray receiver. For example, because of the axis positions of the robot during its motion, it is possible for the control device to update the (three-dimensional) 3D model of the robot with carrying device to the current orientation in space.

In addition, the 3D model models the spatial extension of the additional device and/or of a living organism, which is for example the living organism of which the X-ray image or images are being recorded, or some other living organism such as an attending doctor. It is thus possible for the control device to detect a potential collision of the X-ray device with the additional device of the medical workstation and/or with the living organism in advance on the basis of the 3D model, and to initiate the action to prevent the potential collision. This action includes for example emergency braking of the motion of the robot, decelerating its motion, or changing its trajectory in order to avoid the living organism and/or the device.

According to one variant of the X-ray device according to the invention, in which the additional device is the height-adjustable patient table, the control device of the robot is coupled with the patient table in order to update the part of the 3D model that models the patient table when the height of the patient table is adjusted. The patient table is designed for example in such a way that it conveys to the control device an electrical signal assigned to its current height, on the basis of which the control device is able to update the part of the 3D model that models the patient table. The patient table can also be height-adjustable by means of a computer, and can be coupled with that computer in order to obtain information about the current height of the patient table. That enables a potential collision of the X-ray device according to the invention with the patient table to be better avoided.

Another aspect of the invention relates to an additional medical workstation, having
- an X-ray device having a robot with a plurality of axes, with a control device that is set up to actuate the axes for a motion of the robot, and with an attaching device and a carrying device situated on the attaching device, having an X-ray source and an X-ray receiver,
- an additional robot, which has a plurality of axes, a control device that is set up to actuate the axes for a motion of the additional robot, and an additional attaching device,
- a patient table situated on the additional attaching device, and
- a computing device in which a 3D model of the medical workstation is stored, which models the spatial extension of the robot with positioned carrying device while the robot is in motion and the spatial extension of the additional robot with positioned carrying device while the additional robot is in motion, and the computing device detects a potential collision of the X-ray device with the additional robot and/or with the patient table on the basis of the 3D model and causes the two robots to initiate an action to prevent the potential collision.

Accordingly, the additional workstation according to the invention has essentially the X-ray device according to the invention and also the additional robot, to whose attaching device, which is for example a flange, the patient table is attached. Accordingly, the position and/or orientation of the patient table in space can be changed by means of the additional robot.

The additional medical workstation also has the computing device in which the 3D model of the workstation is stored. The computing device can be separate from the two control devices and coupled with the two control devices of the two robots, so that the 3D model of the additional medical workstation can be updated while the robots are in motion. It is also possible, however, that one of the two control devices includes the computing device, in which case the two control devices are coupled with each other. In this case, the 3D model of the additional medical workstation is stored in the corresponding control device. It is also possible, however, for the 3D model of the medical workstation to be stored in both control devices. Because of the coupling of the control devices, the 3D model or models can be adapted to the motion of the robots.

In order to also at least reduce the danger of a collision of the robots with a living organism present within the additional workstation, according to one variant of the additional medical workstation according to the invention, the 3D model also models at least one living organism present within the workstation, and the computing device is set up to detect a potential collision of the X-ray device, the additional robot and/or the patient table with the living organism on the basis of the 3D model and to cause the two robots to initiate an action to prevent the potential collision.

According to one variant of the X-ray device according to the invention, the latter has at least one sensor coupled with the control device, which sensor is set up to detect a motion of the additional device and/or a motion of the living organism, in order to update the current position of the additional device and/or of the living organism in the 3D model. The surroundings of the X-ray device according to the invention can be registered by means of the at least one sensor. This is advantageous for example when a motion or a change of the position of the additional device of the medical workstation cannot be planned or predicted. By means of the signals coming from the sensor, it is then possible to update the 3D model accordingly. The use of the at least one sensor is also suitable for monitoring the living organism, in particular when the latter is moving. If the living organism is a patient, in particular lying on the patient table, of whom the X-ray device according to the invention is supposed to produce an X-ray image, then in this way at least the danger of a collision with the living organism can be reduced if the latter for example moves unexpectedly. The sensor can be for example an optical sensor, by means of which the position and/or motion of the living organism (or of the additional device of the medical workstation) is registered.

The sensor used can be for example a contact sensor, a near field sensor and/or a wide field sensor.

If a plurality of sensors for example are used, then a measuring range monitored by the sensors can be subdivided as follows:

Contact sensors, which may for example take the form of relatively simple switches that react to pressure (such as safety switch strips, pressure-sensitive mats), permit a yes/no decision and are able to bring the robot to a safe state. Motor currents and moment sensors, for example in the joints, the structure, the drives, etc. of the robot, make it possible to measure interaction forces between the robot and its surroundings. An appropriate reaction of the robot can then be initiated.

Near field sensors, such as capacitive sensors, can detect a change in the electric field of the sensor surroundings at a distance of up to some decimeters. Based on this change, a conclusion can be drawn for example about the position of the living organism and/or of the additional device.

Wide field sensors, such as a camera, in particular one that is suitable for recording a three-dimensional image, light barriers or laser scanners allow wide-ranging protection of the working zone of the robot.

Examples of exemplary embodiments of the invention are depicted in the accompanying schematic drawing. The figures show the following:

FIG. 1 a medical workstation with an X-ray device, and

Figure 2:
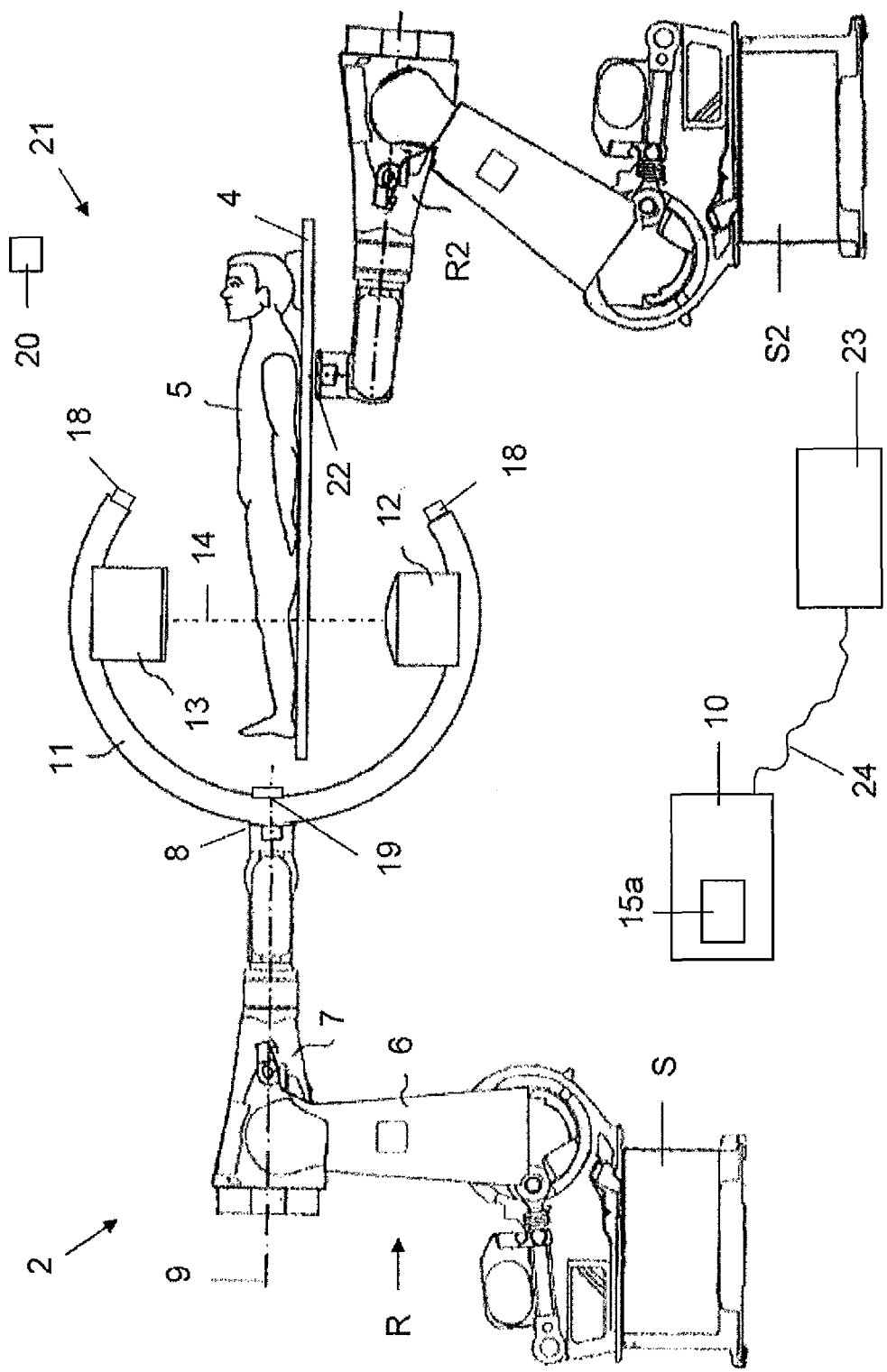

FIG. 2 an additional medical workstation with an X-ray device.

FIG. 1 shows a medical workstation with an X-ray device 2 and a patient table 4, which in the case of the present exemplary embodiment is height-adjustable by means of a lifting device 3. Patient table 4 is provided so that a living organism 5 can lie on it for an examination with X-ray device 2.

X-ray device 2 has a robot R with kinematics for motions in for example six degrees of freedom. Robot R has, in a generally known manner, six axes of motion, joints, levers 6, 7 and a flange 8. FIG. 1 shows only one of the axes of motion, with the reference label 9. In the case of the present exemplary embodiment, robot R is attached to a base S.

Each of the axes of motion 9 is moved by a drive, not shown in greater detail. Each of the drives includes for example an electric motor and gears, as generally known to a person skilled in the art. Robot R also has a control computer 10, which is connected with the drives of the robot R in a manner not shown and controls them in a generally known way by means of a computer program running on control computer 10, so that flange 8 of robot R executes a predefined motion.

X-ray device 2 also has a carrying device, which in the case of the present exemplary embodiment is designed as a C-shaped arc, attached to flange 8 of robot R. An X-ray source 12 and an X-ray receiver 13 are situated opposite each other on C-shaped arc 11. In the case of the present exemplary embodiment, X-ray receiver 13 is a solid-state detector which is known per se. However, X-ray receiver 13 can also be an X-ray image intensifier. When X-ray device 2 is in operation, an X-ray beam whose central beam 14 is depicted in FIG. 1, emitted by X-ray source 12 and attenuated as it passes through living organism 5, strikes X-ray receiver 13. X-ray receiver 13 converts the incident X-ray beam in a generally known manner into an electrical signal, which is assigned to an X-ray image of living organism 5, which is not shown in further detail in the figures and which can be depicted by means of a display device which is also not shown in further detail in the figures.

When X-ray device 2 is in operation, C-shaped arc 11 can be moved by robot R, in particular on a predefined path.

In the case of the present exemplary embodiment, a three-dimensional (3D) model 15 of medical workstation 1 is stored on control computer 10 of robot R. The 3D model 15 models the spatial extension of X-ray device 2, i.e., the spatial extension of robot R with C-shaped arc 11 attached to it, including in particular while robot R is in motion. An update of 3D model 15 while robot R is in motion results for example from signals from angle sensors, which are not shown in further detail in the figures but are known to a person skilled in the art, which measure the current angles of the axes of motion 9.

In the case of the present exemplary embodiment, 3D model 15 also models the patient tables 4 and their lifting device 3. Lifting device 3 includes for example an electric drive 16, with which the height of patient table 4 can be adjusted. Electric drive 16 is connected in the case of the present exemplary embodiment by an electrical cable 17 to control computer 10, so that control computer 10 is not only able to update the part of 3D model 15 that models X-ray device 2 on the basis of a motion of robot R, but is also able to update the part of 3D model 15 that models patient table 4 with lifting device 3 on the basis of an adjustment to the height of patient table 4.

In the case of the present exemplary embodiment, 3D model 15 also models the living organism 5 lying on patient table 4, it being possible to input the size of the living organism into control computer 10, in order to adapt 3D model 15 to the living organism currently lying on patient table 4. In addition, it is possible to specify the position in which living organism 5 is supposed to be located in relation to patient table 4: in particular whether living organism 5 is lying on patient table 4.

In the case of the present exemplary embodiment, a computer program is running on control computer 10, which checks on the basis of 3D model 15 of medical workstation 1 whether a potential collision of X-ray device 2 with patient table 4, lifting device 3 or living organism 5 is imminent, based on the current motion of robot R, the position of patient table 4 and the position of C-shaped arc 11. If the computer program detects such a potential collision, then control computer 10 automatically initiates an appropriate action in order to prevent the potential collision, or at least to lessen its negative effect. An appropriate action is for example emergency braking of robot R, or a change to the planned motion of robot R to prevent the collision.

In the case of the present exemplary embodiment there are two contact sensors 18 situated on C-shaped arc 11, which are connected to control computer 10 in a manner not shown. If one of the contact sensors 18 comes into contact with an object, for example patient table 4 or the living organism 5 lying on patient table 4, then control computer 10 automatically causes robot R to stop moving.

Also situated on C-shaped arc 11 in the case of the present exemplary embodiment is a capacitive sensor 19, which is connected to control computer 10 in a manner not shown, which detects a change in an electrical field in the vicinity of capacitive sensor 19. Based on the detected change in the electrical field, on the height setting of patient table 4 and of modeled living organism 5, control computer 10 is also able, among other things, to detect a change in the position of living organism 5, to detect a potential collision of X-ray device 2 with living organism 5 if appropriate, and if necessary to initiate the action to prevent the potential collision. Based on the detected change in the electrical field, it is also possible for control computer 10 to detect a potential collision with another object or another living organism, in order to initiate the action to prevent the potential collision if necessary.

Medical workstation 1 in the case of the present exemplary embodiment has another 3D sensor 20, which is connected to control computer 10 in a manner not shown. 3D sensor 20 is provided to produce a three-dimensional image of medical workstation 1, in particular in order to detect a motion of living organism 5. On the basis of the detected motion of living organism 5, control computer 10 is able to update the part of the 3D model that models living organism 5, which makes it possible to better detect a potential collision of X-ray device 2 with living organism 5.

FIG. 2 shows an additional medical workstation 21. Unless described otherwise below, components of medical workstation 21 that are essentially the same in function and construction as components of medical workstation 1 shown in FIG. 1 are given the same reference label.

The medical workstation 21 shown in FIG. 2 differs essentially from the medical workstation 1 shown in FIG. 1 in that the patient table is also height-adjustable, among other things, not by means of lifting device 3 but by means of a robot R2. Robot R2 is similar in construction to robot R, and has kinematics for motions in for example six degrees of freedom. Robot R2 has, in a generally known manner, six axes of motion, joints, levers and a flange 22, and in the case of the present exemplary embodiment is attached to a base S2. Patient table 4 is attached to flange 22 of robot R2, so that robot R2 is able to change the position of patient table 4.

Each of the axes of motion of robot R2 is moved by a drive, not shown in greater detail. Each of the drives includes for example an electric motor and gears, as generally known to a person skilled in the art. Robot R2 also has a control computer 23, which is connected with the drives of the robot R2 in a manner not shown and controls them in a generally known way by means of a computer program running on control computer 23, so that flange 22 of robot R2 executes a predefined motion.

A 3D model 15a of medical workstation 21 is stored in control computer 10 of robot R. In the case of the present exemplary embodiment, this 3D model 15 models the spatial extension of X-ray device 2, i.e., the spatial extension of robot R with C-shaped arc 11 attached to it, including in particular while robot R is in motion. 3D model 15a also models patient tables 4 and robot R2 in a corresponding manner, i.e., their spatial extensions, even while robot R2 is in motion. In order for control computer 10 of robot R to be able to update the part of 3D model 15a that models robot R2 with patient table 4, the two control computers 10, 23 are connected by means of a data line 24. Consequently control computer 10 of robot R is able to obtain information about the current angular positions of robot R2 from control computer 23 of robot R2, and to update 3D model 15a on the basis of this information.

In the case of the present exemplary embodiment, 3D model 15a also models the living organism 5 lying on patient table 4, it being possible to input the size of the living organism into control computer 10, in order to adapt 3D model 15a to the living organism 5 currently lying on patient table 4. In addition, it is possible to specify the position in which living organism 5 is located in relation to patient table 4: in particular whether living organism 5 is lying on patient table 4.

In the case of the present exemplary embodiment, there is also a computer program running on control computer 10, which checks on the basis of 3D model 15a of medical workstation 21 whether a potential collision of X-ray device 2 with patient table 4, robot R2 or living organism 5 is imminent, based on the current motions of robots R, R2, the position of patient table 4 and the position of C-shaped arc 11. If the computer program detects such a potential collision, then control computer 10 automatically initiates an appropriate action in order to prevent the potential collision, or at least to lessen its negative effect. An appropriate action is for example emergency braking of robots R, R2, or a change to the planned motions of robot R, R2 to prevent the collision.

Medical workstation 21 in the case of the present exemplary embodiment has the contact sensors 18 situated on C-shaped arc 11, the capacitive sensor 19 situated on C-shaped arc 11, and the 3D sensor 20, whereby a potential collision of X-ray device 2 with living organism 5 can be better detected.

Alternatively, 3D model 15a of medical workstation 21 can also be stored in control computer 23 of robot R2. It is also possible for 3D models 15a of medical workstation 21 to be stored in both control computers 10, 23, whereby redundant monitoring of a potential collision is made possible. The 3D model 15a of workstation 21 can also be stored in an external computer, which is connected to the control computers 10, 23 of the two robots R, R2, and which actuates control computers 10, 23 when a potential collision is detected in such a way that they initiate an action to prevent the potential collision.

The invention claimed is:

1. A medical workstation, comprising:
   a robot having a plurality of articulation axes and an end flange for supporting an attachment;
   a carrier operatively coupled to said end flange for movement therewith;
   an x-ray source and an x-ray receiver supported on said carrier;
   a three-dimensional model that models the position and spatial extent of said carrier during movement of said robot, and that models the position and spatial extent of at least one of an additional device or a living organism; and
   a control utilizing said three-dimensional model and actuating said robot to prevent a collision of said carrier, said x-ray source, or said x-ray receiver with the additional device or the living organism during movement of said robot.

2. The medical workstation of claim 1, further comprising:
   at least one sensor communicating with said control, said sensor detecting a motion of at least one of the additional device or the living organism;
   said control updating said three-dimensional model to reflect a current position of at least one of the additional device or the living organism in response to the motion detected by said at least one sensor.

3. The medical workstation of claim 2, wherein said at least one sensor comprises a contact sensor, a near field sensor, or a wide field sensor.

4. The medical workstation of claim 1, wherein said additional device comprises a height-adjustable patient table.

5. The medical workstation of claim 4, wherein said control is operatively coupled with said height-adjustable patient table, said control configured to update the position of said patient table in said three-dimensional model when a height of said patient table is adjusted.

6. A medical workstation, comprising:
   a first robot having a plurality of articulation axes and an first end flange for supporting an attachment;
   a carrier operatively coupled to said first end flange for movement therewith;
   an x-ray source and an x-ray receiver supported on said carrier;
   a second robot having a plurality of articulation axes and an second end flange for supporting an attachment;
   a patient support operatively coupled to said second end flange for movement therewith;
   a three-dimensional model that models the position and spatial extent of said first robot and said carrier during movement of said first robot, and modeling the position and spatial extent of said second robot and said patient support; and
   a control utilizing said three-dimensional model and actuating said first and second robots to prevent a collision of said carrier, said x-ray source, or said x-ray receiver with said second robot or said patient support during movement of at least one of said first and second robots.

7. The medical work station of claim 6, wherein said control comprises a first control actuating said first robot and a second control actuating said second robot, said first control in communication with said second control.

8. The medical workstation of claim 6, wherein;
   said three-dimensional model further models a position and extend of at least one living organism present within the medical workstation; and
   said control actuates said first and second robots to prevent a collision of said carrier, said x-ray source, or said x-ray receiver with said living organism during movement of at least one of said first and second robots.

9. The medical workstation of claim 6, further comprising:
   at least one sensor communicating with said control, said sensor detecting a motion of the living organism;

said control updating said three-dimensional model to reflect a current position of the living organism in response to the motion detected by said at least one sensor.

10. The medical workstation of claim 9, wherein said at least one sensor comprises a contact sensor, a near field sensor, or a wide field sensor.

\* \* \* \* \*

UNITED STATES PATENT AND TRADEMARK OFFICE
CERTIFICATE OF CORRECTION

PATENT NO. : 8,548,629 B2  Page 1 of 1
APPLICATION NO. : 12/988178
DATED : October 1, 2013
INVENTOR(S) : Tobias Ortmaier et al.

It is certified that error appears in the above-identified patent and that said Letters Patent is hereby corrected as shown below:

In the Specification:

Column 4
Line 61 reads "accompanying schematic drawing." and should read -- accompanying schematic drawings. --.

In the Claims:

Claim 6, Column 8,
Lines 30-31 reads "and an first end flange for" and should read -- and a first end flange for --.

Claim 6, Column 8,
Lines 36-37 reads "and an second end flange for" and should read -- and a second end flange for --.

Claim 8, Column 8,
Line 54 reads "of claim 6, wherein;" and should read -- of claim 6, wherein: --.

Claim 8, Column 8,
Line 56 reads "and extend of at least one" and should read -- and extent of at least one --.

Signed and Sealed this
Twenty-ninth Day of April, 2014

Michelle K. Lee
*Deputy Director of the United States Patent and Trademark Office*